(12) United States Patent
Kemps (10) Patent No.: US 9,919,126 B2
(45) Date of Patent: Mar. 20, 2018

(54) BREATHING ASSISTANCE APPARATUS

(71) Applicant: FISHER & PAYKEL HEALTHCARE LIMITED, Auckland (NZ)

(72) Inventor: David Kemps, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 581 days.

(21) Appl. No.: 14/411,084

(22) PCT Filed: Jun. 24, 2013

(86) PCT No.: PCT/NZ2013/000111
§ 371 (c)(1),
(2) Date: Dec. 23, 2014

(87) PCT Pub. No.: WO2014/003578
PCT Pub. Date: Jan. 3, 2014

(65) Prior Publication Data
US 2015/0151075 A1    Jun. 4, 2015

Related U.S. Application Data

(60) Provisional application No. 61/665,191, filed on Jun. 27, 2012.

(51) Int. Cl.
*A61M 16/00* (2006.01)
*A61M 16/20* (2006.01)
(Continued)

(52) U.S. Cl.
CPC ...... *A61M 16/201* (2014.02); *A61M 16/0057* (2013.01); *A61M 16/0463* (2013.01);
(Continued)

(58) Field of Classification Search
CPC .............. A61M 16/0463; A61M 16/20; A61M 2205/3331; A61M 2240/00;
(Continued)

(56) References Cited

U.S. PATENT DOCUMENTS 3,799,185 A * 3/1974 Milnes ................. F16K 15/148
137/102
4,239,038 A    12/1980 Holmes
(Continued)

FOREIGN PATENT DOCUMENTS

WO    WO 1999/059517    11/1999
WO    WO 2003/066146    8/2003

OTHER PUBLICATIONS

PCT International Search Report; Application No. PCT/NZ2013/000111; Filed Jun. 24, 2013.

*Primary Examiner* — Rachel T Sippel
*Assistant Examiner* — Douglas Sul
(74) *Attorney, Agent, or Firm* — Knobbe, Martens, Olson & Bear, LLP (57) ABSTRACT

A pressure regulating device for use with a breathing assistance and/or resuscitation apparatus, which conveys gases along a gases pathway to a patient, includes a mounting for connecting the pressure regulating device to a first outlet in fluid communication with the gases pathway. The mounting holds a valve member that selectively blocks, at least in part, the first outlet. A control member can be manipulated to adjust a property of the valve member. The valve member at least partially blocks the first outlet when the pressure of gases in the pathway is below a selected level, and allows at least a portion of the gases to flow out of the first outlet when the pressure of said gases is above the selected level. The property includes a selected level of pressure whereby manipulation of the control member adjusts the level of pressure between a maximum level and a minimum level.

42 Claims, 6 Drawing Sheets

(51) Int. Cl.
  *A61M 16/04*    (2006.01)
  *A61M 16/16*    (2006.01)
  *A61M 16/06*    (2006.01)
  *A61M 16/08*    (2006.01)

(52) U.S. Cl.
  CPC ............ *A61M 16/06* (2013.01); *A61M 16/16* (2013.01); *A61M 16/20* (2013.01); *A61M 16/206* (2014.02); *A61M 16/209* (2014.02); *A61M 16/0816* (2013.01); *A61M 2016/003* (2013.01); *A61M 2202/0488* (2013.01); *A61M 2205/3331* (2013.01); *A61M 2240/00* (2013.01)

(58) Field of Classification Search
  CPC ...... A61M 2016/003; A62B 7/04; A62B 9/02; A62B 9/022; A62B 18/10; Y10T 137/7878; Y10T 137/7906; Y10T 137/789
  USPC .................................................. 137/510, 524
  See application file for complete search history.

(56) References Cited

U.S. PATENT DOCUMENTS

| | | | | |
|---|---|---|---|---|
| 4,257,453 | A * | 3/1981 | Kohnke | A61M 16/208 137/514.3 |
| 5,109,840 | A * | 5/1992 | Daleiden | A61M 16/208 128/204.28 |
| 6,619,308 | B2 * | 9/2003 | Massengale | G05D 16/0647 137/12 |
| 6,691,735 | B1 * | 2/2004 | Harneit | F16K 37/0008 137/505 |
| 7,341,059 | B2 * | 3/2008 | Moody | A61M 16/00 128/204.18 |
| 2004/0040559 | A1 | 3/2004 | Moody et al. | |
| 2012/0012111 | A1 * | 1/2012 | Howe, Jr. | A61M 16/1055 128/205.12 |

* cited by examiner

BREATHING ASSISTANCE APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The invention relates to the use of a pressure regulator in conjunction with a breathing assistance apparatus, particularly though not solely, for regulating the pressure of gases supplied to a patient from a Positive End Expiratory Pressure (PEEP) apparatus or for a patient resuscitation device.

At the moment of their first breath, a baby's lungs are collapsed and filled with fluid. The pressures needed to open their lungs and keep them open are several times that of a normal breath until the fluid is displaced and the lungs have filled with air. To generate these large pressures, the baby must have strong respiratory muscles, as well as a surfactant in their alveoli. The surfactant reduces the surface tension of the fluid within the alveoli, preventing the alveolar walls from sticking to each other.

Neonates have difficulty in opening their lungs and keeping them open. Reasons for this include:

a) Weak respiratory muscles and low surfactant levels resulting in insufficient pressure to open the lungs and, should they be resuscitated, quick tiring from the effort of keeping the alveoli open.

b) Underdeveloped internal tissue structure to support the alveoli.

c) Slower clearance of lung fluid. In very premature neonates, fluid may continue to be secreted in the alveoli even after birth.

d) A soft chest wall, horizontal ribs, and a flatter diaphragm contribute to reduce the inspiratory capacity.

e) The mixing of oxygenated and deoxygenated blood raises blood pressure in the lungs, increasing fluid movement from the blood vessels into the lung tissue. The reduced blood oxygen level starves tissue of oxygen, weakening respiratory muscles.

f) Weak neck muscles and a lack of neck fat reduce upper airway stability so that collapse on inspiration may occur.

g) Collapsed, damaged alveoli secrete proteins that reduce surfactant function.

To alleviate this it is known to apply Positive End Expiratory Pressure (PEEP) during respiration, resuscitation or assisted respiration (ventilation). In applying PEEP, the patient's upper airway and lungs are held open during expiration against a pressure that stops alveolar collapse. Lung fluid is pushed back into the circulating blood, alveolar surfactant is conserved, and a larger area of the lung participates in gas exchange with the blood. As blood oxygenation and carbon dioxide removal improves, more oxygen is delivered to growing tissue, while less oxygen and energy is consumed by respiratory muscles. In the case of resuscitation or ventilation the pressure is varied between a Peak Inspiratory Pressure (PIP) and the PEEP value until the patient is breathing spontaneously.

To provide the PEEP across a range of flow rates, some method is required to regulate the pressure to prevent injury to patients, particularly neonates due to the fragility of their lungs and airway.

It is known to provide a valve near the patient which actuates at a level of pressure (namely, the PEEP value) to allow the gases to vent externally and reduce pressure in the stream delivered to the patient. Such valves may be spring-loaded. These require the use of high quality springs which must be individually tested to give a high tolerance spring constant to ensure that they actuate at a value substantially that of the maximum safe pressure. Both the manufacture and testing of such a spring result in high costs. Also such valves are known to have substantial variation of the relief pressure with flow rate.

To address issues with spring-loaded valves, umbrella valves have been used. Umbrella valves provide a lower variation in delivered pressure.

US 2004/0040559, which is incorporated herein by reference, discloses umbrella valve designs for reducing the variation in delivered pressure that may be experienced with prior art valves. According to particular embodiments, the elastomeric member used to selectively close the vent is adapted such that as the flow rate increases, a larger portion of the flow at the inlet is able to pass through the vent, better regulating the pressure delivered to the patient.

Figures 1, 2:
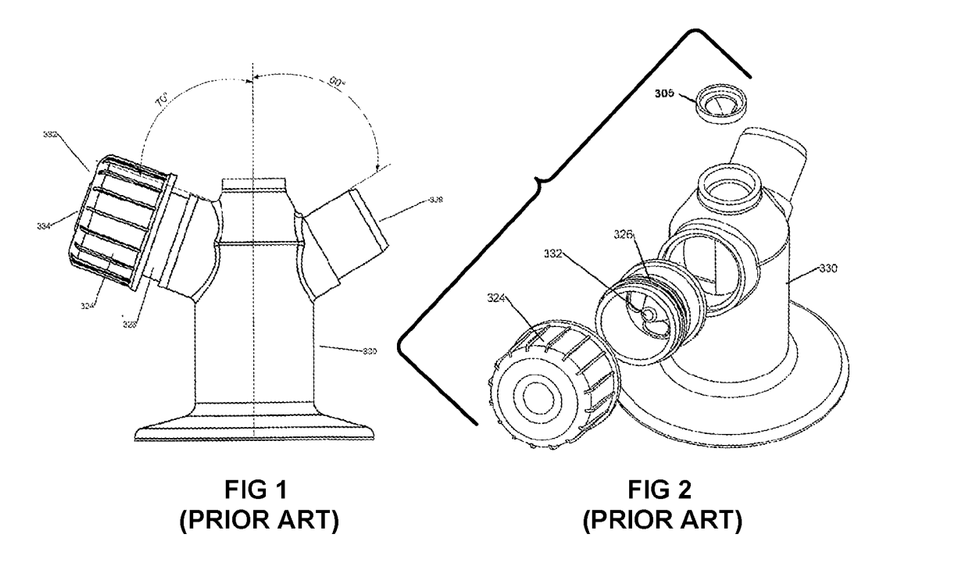
FIGS. 1 & 2 show side and exploded perspective views, respectively, of a prior art adjustable relief valve.

US 2004/0040559 further describes an arrangement which enables the PEEP value to be manually adjusted. This arrangement is shown in FIGS. 1 and 2. Referring to FIGS. 1 and 2, gas enters the apparatus 330 via inlet 328 and generally exits via an outlet (in the base of apparatus 330 but hidden in the Figures provided) which couples to a mask or other patient interface (not shown) to deliver air to the patient, typically an infant. The apparatus 330 further includes a vent which terminates in an orifice 334 in a screw on cap 324 which engages with thread 326 on the main body of the apparatus 330. Air exits through the vent via nozzle 332 and apertures positioned around the nozzle 332. As will be appreciated, due to the position of the nozzle 332 in relation to the orifice 334, rotation of the cap on the thread 326 will not significantly affect flow through the nozzle 332. However, rotation of the cap 324 does affect flow from the apertures around the nozzle 332 because as the cap is tightened, the orifice 334 becomes partially blocked by the outer wall of the nozzle 332, reducing flow. Thus, rotation of the cap 324 enables the PEEP value to be adjusted.

Figure 3:
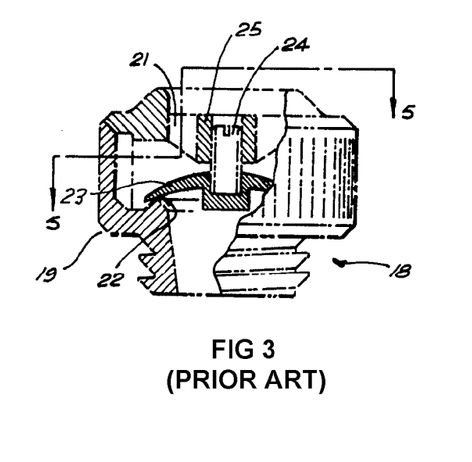
FIGS. 3 & 4 show partial cut-away side and end views, respectively of another prior art adjustable relief valve.
Figure 4:
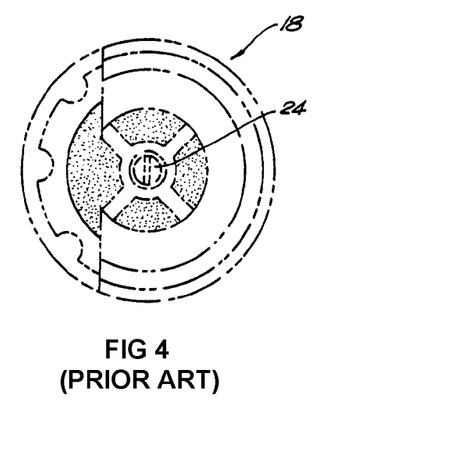

U.S. Pat. No. 4,239,038 describes a relief valve assembly for relieving excess pressure in a manual resuscitator that may result from a user exerting too much force to compress a self-inflating bag type reservoir of the resuscitator. The assembly includes a vent (generally similar to that shown in US 2004/0040559) that is adjacent an outlet for interfacing with a patient. According to one embodiment, as shown in FIGS. 3 and 4 herein, the valve assembly includes a threaded portion 18 for connecting to the resuscitator. Valve element 23 is biased against a seat 22 to seal the opening. In the event there is excessive pressure in the resuscitator, the valve element 23 moves upwards and away from the seat, allowing gas to be vented through aperture 21.

According to one embodiment described in U.S. Pat. No. 4,239,038, the valve element 23 is mounted on a screw 24 via the end wall 25 of the cap whereby rotation of the screw 24 adjusts the force with which the valve element 23 bears against the seat 22, thereby adjusting the adjusting the pressure at which the valve assembly provides relief. While this provides adjustment of the relief pressure, a screwdriver or other like tool is required to do so. Further, overtightening of the screw 24 may urge the valve member 23 too far downwards such that valve member 23 and screw 24 become detached from the cap. This could result in portions of the assembly being passed to the patient interface outlet with the potential risk of injury to a patient. Conversely, withdrawing the screw 24 too far from the cap may urge the valve member 23 into contact with the end wall 25 of the cap potentially damaging the valve member 23. This may affect performance of the valve assembly and again potentially result in parts of the apparatus (i.e., fragmented parts of the valve element 23) being passed to the patient interface.

It is an object of the invention to provide apparatus which overcomes or ameliorates at least one problem associated with prior art arrangements.

Alternatively, it is an object of the invention to at least provide a useful choice to the public.

SUMMARY OF THE INVENTION

According to a first aspect of the invention, there is provided a pressure regulating device for use with a breathing assistance and/or resuscitation apparatus which conveys gases along a gases pathway to a patient, particularly an infant or neonate and more particularly a prematurely born neonate but not limited thereto, the device comprising:
- a mounting for connecting the pressure regulating device to a first outlet in fluid communication with the gases pathway, the mounting configured to hold a valve member that selectively blocks, at least in part, the first outlet;
- a control member moveably engaged with the mounting wherein manipulation of the control member adjusts a property of the valve member,
- wherein the valve member is configured to at least partially block the first outlet when the pressure of gases in the pathway is below a selected level, and allow at least a portion of said gases to flow out said first outlet when the pressure of said gases is above said selected level, and
- wherein said property comprises said selected level whereby manipulation of the control member adjusts the level of pressure between a maximum level and a minimum level at which the valve member allows at least a portion or an increased portion of said gases to flow out of said first outlet.

Preferably the control member is capable of manipulation by hand, without the need for use of additional equipment such as a screwdriver.

Preferably the control member is rotatably coupled to the mounting.

Preferably the control member is otherwise fixed relative to the mounting although it may be detachable therefrom.

Preferably the valve member comprises an elastomeric member. More preferably the valve member is integrally molded from liquid silicon.

Preferably the valve member comprises a skirt or at least one flap wherein said selective blocking is performed by movement of the skirt or flap(s). Where multiple flaps are used, these may, for example, take the form of radially extending lobes.

Preferably the valve member comprises a shaft.

Preferably the shaft is joined to or integral with the skirt or flap(s).

Preferably the shaft is substantially perpendicular to the skirt or flap(s) and/or centrally positioned in relation thereto.

Preferably the thickness of the flap proximate to the join with the shaft is less than the thickness of the skirt or flap(s) at the periphery thereof. More preferably the ratio of thicknesses is substantially 2:3.

Preferably the valve member is an umbrella valve. However, other valve means may be used including membranes otherwise fixed in position to selectively close, at least partially, the first outlet.

Preferably the mounting comprises framework for defining an aperture in which the shaft of the valve member is received and held.

Preferably the valve member is held in a substantially central position in the first outlet with respect to a plane substantially perpendicular to flow through the first outlet when the first outlet is open.

Preferably the pressure regulating device comprises a seat member, the seat member being positioned such that when the pressure of gases is below the selected level, a portion of the valve member sits thereon.

Preferably the seat member comprises a substantially annular surface on which said portion of the valve member sits.

Preferably the seat member is engaged with the control member whereby manipulation of the control member moves the seat member and effects said adjustment of the selected level of pressure.

Preferably the pressure regulating device is configured such that manipulation of the control member moves the seat member in a direction substantially parallel to the normal flow of gases through the first outlet when the first outlet is open.

Preferably the control member is rotatably fixed relative to the seat member. More preferably the seat member comprises at least one projection configured to engage at least one projection or recess in the control member to effect said rotational fixing although alternative arrangements may be used.

Preferably the seat member is threadingly engaged to said mounting whereby rotation of the control member effects said movement of the seat member.

Preferably engagement between the control member and seat member provides for sliding engagement, preferably in a direction substantially parallel to the normal flow of gases through the first outlet when the first outlet is open.

To this end, according to one embodiment, the seat member comprises at least one projection configured to be received in a groove or between elongated teeth provided on the control member, the projection being slidable along the groove or between the teeth but preventing relative rotation between the control member and the seat member. As will be appreciated, alternatively, a groove or grooves in the seat member may similarly engage with projection(s) or teeth on the control member.

Preferably the control member is in the form of a cap and comprises a sidewall that extends from the first outlet when coupled thereto.

Preferably the cap comprises an orifice.

Preferably the orifice is configured to be selectively occluded such as by placement of a finger or thumb of a user thereon. Such operation preferably varies the pressure of gases in the pressure regulating device between a desired PIP and PEEP by occluding or not, respectively the orifice.

Preferably, with the control member in any given position, the pressure of gases inside the gases pathway is substantially independent of the rate of flow of gases along the pathway.

Thus preferred embodiments of the pressure regulating device of the first aspect provide a vent that provides for controlled and adjustable pressure relief so that when coupled to a breathing circuit, the pressure of gases delivered to a patient is substantially constant or independent or gases flow rate but manually adjustable to different levels by manipulation of the control member.

Preferably the pressure regulating device comprises the first outlet.

The mounting may be integral with or coupleable (preferably sealably) to a wall defining the first outlet.

Preferably the pressure regulating device comprises an inlet for receiving gases therethrough.

The inlet is preferably configured to couple to apparatus configured to provide a flow of gas. The apparatus may comprise a pump and/or a humidifier and may be coupled via known conduits.

Preferably the pressure regulating device comprises a second outlet, the second outlet configured to deliver gas to patient.

The second outlet may form part of a patient interface such as a mask.

Alternatively, the second outlet may be configured to couple (preferably sealably) to a patient interface, including via intermediate equipment such as a conduit.

More particularly, the pressure regulating device preferably comprises a housing that defines the inlet, the first outlet and the second outlet.

The inlet and the first and second outlets are all in fluid communication. When the first outlet is blocked or substantially blocked, at least a major portion of the gas entering the inlet is delivered to a patient interface via the second outlet. When the valve member opens, at least a portion of the gas is vented through the first outlet thereby providing pressure relief.

According to particular embodiments, the housing comprises an aperture adapted to allow insertion of equipment therethrough, such as surfactant delivery means or a suction tube.

Preferably the pressure regulating device comprises a sealing means adapted to prevent gas flow through said aperture and allow the equipment to be inserted therethrough while providing breathing assistance.

Preferably the sealing means is a duck billed valve.

Preferably said aperture and said second outlet are substantially aligned or coaxial.

In a further aspect there is provided a pressure regulator for use with a breathing assistance and/or resuscitation apparatus, and which is arranged to regulate pressurised gases supplied to a patient by releasing or exhausting some gases when the pressure exceeds a threshold. This threshold is preferably easily manipulated by manual adjustment of the regulator by a user's digits including fingers and/or thumbs. In an embodiment this is achieved by adjusting the position of a valve seal against which a valve member is biased.

In an embodiment there is provided a pressure regulator for a breathing assistance apparatus and comprising: a mounting having an inlet port for receiving pressurised gases, an outlet port for delivering said pressurised gases to a patient, and a relief port for regulating the pressure of said gases; the relief port including a valve member biased against a valve seat and arranged to open when the pressure of said gases exceeds a selected level in order to release some of the gases out through the relief port; wherein the position of the valve seat is manually adjustable within the relief port in order to adjust the selected level of pressure at which the valve member will open.

In an embodiment the pressure regulator further comprises a control interface adapted to operate under manual digital manipulation by a user, the control interface externally mounted on the mounting and arranged to adjust the position of the valve seat in response to relative movement between the interface and the mounting caused by the digits of the user.

In an embodiment the interface comprises a cap externally mounted over the relief port and which is rotatably moveable thereon.

In an embodiment the cap comprises an orifice for passing the released gases, the orifice being sized to allow its occlusion by a digit of a user.

In another embodiment there is provided a pressure regulator for a breathing assistance apparatus and comprising: a conduit for receiving and delivering pressurised gases, the conduit having a pressure relief valve comprising a valve member and an adjustable valve seat, the valve seat adjustable to vary the pressure at which the relief valve releases some pressurised gas in order to reduce the pressure of the gases in the conduit; wherein the valve seat is arranged to adjust in response to digital pressure by a user of the regulator.

In an embodiment the pressure regulator further comprises a control interface adapted to operate under manual rotation by the user, the control interface externally mounted on the valve and arranged to adjust the position of the valve seat in response to said rotation.

In an embodiment the interface comprises a cap externally mounted over the valve and having an orifice for passing the released gases, the orifice being sized to allow its occlusion by a digit of the user.

In a further aspect there is provided a breathing assistance and/or resuscitation apparatus having a pressure regulator which is arranged to regulate pressurised gases supplied to a patient by releasing or exhausting some gases when the pressure exceeds a threshold. This threshold is preferably easily manipulated by manual adjustment of the regulator by a user's digits including fingers and/or thumbs. In an embodiment this is achieved by adjusting the position of a valve seal against which a valve member is biased.

In embodiments the pressure regulator employed can be as defined above or in the accompanying claims, or substantially as described herein.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

Embodiments of the invention will now be described, by way of example only, with reference to the accompanying drawings in which.

DETAILED DESCRIPTION OF THE PREFERRED EMBODIMENT

Embodiments of the present invention include a connector for resuscitating a patient, particularly an infant or neonate, more particularly a prematurely born neonate. The delivered pressure is varied between Peak Inspiratory Pressure (PIP) and Peak End Expiratory Pressure (PEEP) by the occlusion of the PEEP outlet. The PEEP outlet provides for variable PEEP, by adjustment. However, at any particular PEEP setting, preferred embodiments of the invention provide for substantially flow independent fixed PEEP. The fixed PEEP valve avoids the need for adjustment as flow changes and provides more effective therapy.

A duck billed valve may be included for suctioning of surfactant delivery during resuscitation.

Preferably, the connector is adapted to one handed use.

Figure 5:
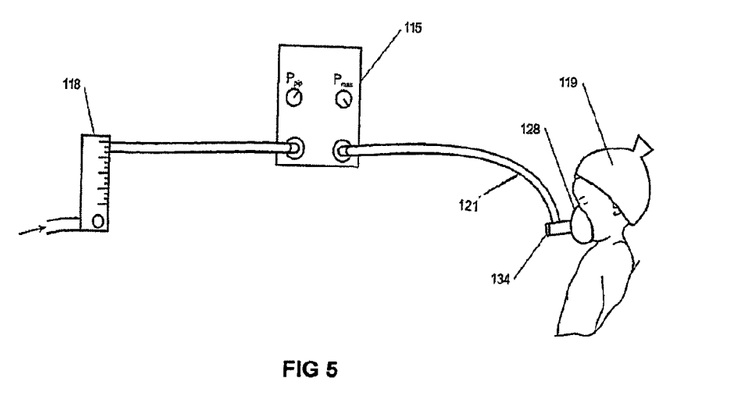
FIG. 5 is a schematic diagram of a typical configuration for supplying breathing assistance to a patient such as a neonate.

Referring now to FIG. 5 in which a typical application is depicted, a Positive End Expiratory Pressure (PEEP) system is shown in which a patient 119, shown as an infant, is receiving pressurized gases through a mask 128 (or endotracheal tube or other interface as are known in the art) connected to an inhalatory conduit 121, preferably for resuscitation. Either the mask 128 or the inhalatory conduit 121 can include the pressure regulator 134 to control the pressure of gas delivered to the patient. The inhalatory conduit 121 is connected to the outlet of a resuscitator apparatus 115, which is in turn connected to a flow regulator and air supply 118 (which preferably provides gas to the resuscitator at 50 psi or thereabouts).

It should be understood that the present invention is not limited to resuscitation, or the delivery of PEEP gases but is also applicable to other types of gas delivery systems, including those adapted to deliver gases to non-infant patients. Further, while embodiments are described showing more sophisticated gas delivery apparatus, it will be appreciated that the invention is not limited to such applications and may also be used with manually powered arrangements, such as those described in U.S. Pat. No. 4,239,038.

A preferred embodiment of apparatus of the invention is shown in FIGS. 6 to 9. According to preferred embodiments, the apparatus is disposed within or coupled to the mask 128 although it will be appreciated that it may form part of a separate assembly provided it is proximate the patient.

Figure 6:
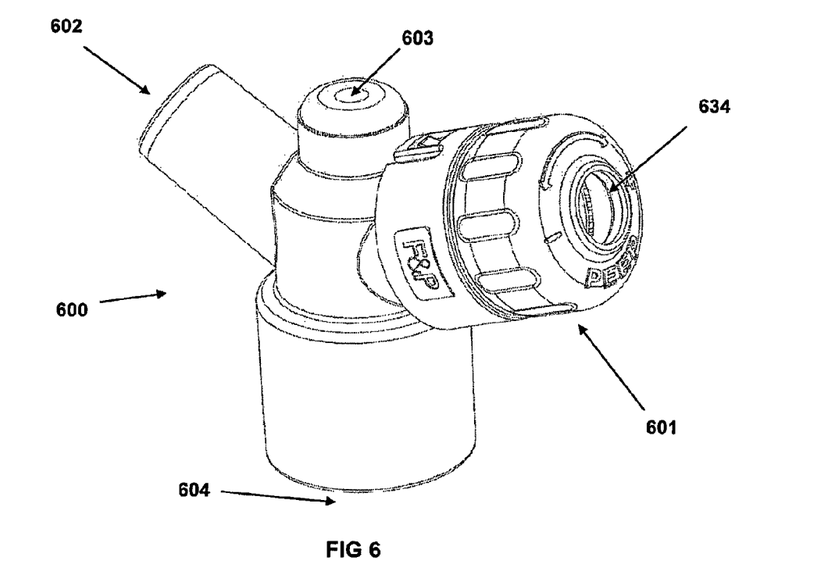
FIG. 6 is a perspective view of a pressure regulator according to an embodiment of the invention.
Figure 7:
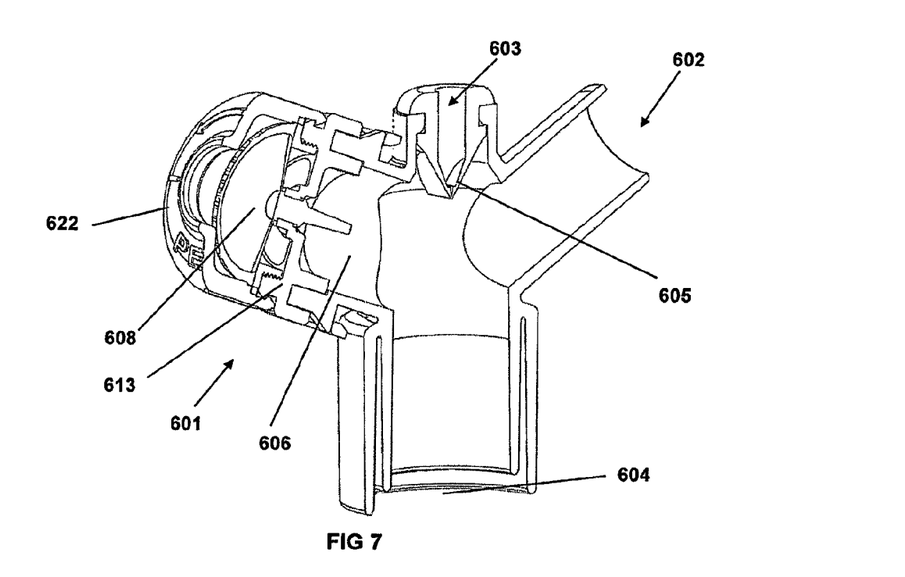
FIG. 7 is a sectional perspective view of the pressure regulator of FIG. 6.

Referring to FIGS. 6 and 7, the apparatus 600 includes an inlet 602 fluidly connected to two outlets 604, 606. The inlet 602 receives gases and delivers these to a patient via a mask or other patient interface (not shown) connected to first outlet 604. The gases may be delivered to the inlet 602 via a flow regulator and air supply 118 and resuscitator 115 as shown in FIG. 5 although other means for delivering pressurised gases may alternatively be used. Further, the gases may simply be air extracted and pumped from the patient's surroundings, and/or may be enriched such as by additionally coupling an oxygen reservoir or supply to the inlet, as is known in the art. Further, the gases may be humidified using known humidifier arrangements.

The second outlet 606 provides an external orifice which terminates a pressure regulator 601. The pressure regulator 601 may be used to vary the pressure between PIP and PEEP by selective occlusion of the orifice 634, such as by placement of a finger over it. A PEEP valve 608 is located between the inlet 602 and the second outlet 604.

The PIP may be adjusted at the resuscitator 115 to a desired level. The delivered gases are varied between the PIP with the orifice 634 near the patient occluded and the PEEP with the orifice 634 unoccluded. In this fashion, resuscitation of a patient can be attempted by varying between the PIP and PEEP at the normal rate of breathing.

The purpose of the PEEP valve 608 of preferred embodiments is to keep the PEEP at a reasonably constant level independent of changes in flow rate. Further, embodiments of the regulator 601 preferably provide for adjustment of the PEEP. Such adjustment may preferably be performed manually without the need for additional equipment or tools, such as a screwdriver.

Desirably for infant respiratory assistance the PEEP value should be approximately 5 cmH2O, independent of the flow rate. Preferably the interface needs to be simple and cost effective, as it is a single-use product. Also, due to the nature of this application, a valve with many small separate parts, such as a spring valve, is not a viable option. Further, as will particularly be appreciated for resuscitation applications, time may be limited and delays caused by complicated adjustment, such as of the PEEP valve described in U.S. Pat. No. 4,239,038, are preferably avoided. Further, while pressurised gas within apparatus 600 will tend to prevent contaminants or debris being passed from the second outlet 606 to the first outlet 604 (and to the patient), the need to insert a tool into the second outlet, as required by U.S. Pat. No. 4,239,038, increases the risk of this happening.

As shown in FIGS. 6 and 7, the apparatus 600 may include a further inlet 603 including a duck billed valve 605 which is normally closed and configured for introducing tubes therethrough and down the trachea for suctioning, delivery of surfactant etc. For the avoidance of doubt, the further inlet 603 may be omitted.

As described in US 2004/0040559, new born neonates often lack surfactant in their lungs. Embodiments of the invention, as shown in FIGS. 6 and 7, when used with an endotracheal tube, make it easy to administer surfactant to a patient without the need to remove the breathing assistance apparatus from the patient. By using a syringe or other device known in the art the operator can administer surfactant to the neonate by pushing the end of the syringe through the duck billed valve 605 located opposite the inlet to the patient (i.e., first outlet 604).

The duck billed valve 605 is normally fluidly sealed but upon insertion of the syringe opens to allow the end of the syringe to enter the interior of the apparatus 600. The bills or flaps of the valve 605 may be formed from silicone rubber or other suitable materials known in the art and they seal around the end of the syringe keeping the apparatus 600 sealed. Because surfactant is a viscous fluid this is advantageous over administering surfactant using multi lumen endotracheal tubes.

The duck billed valve 605 can also be used to suction a neonate to remove airway secretions. Suctioning is performed using a catheter inserted through the duck billed valve and down the endotracheal tube. The bills of the valve seal around the inserted catheter thereby maintaining airway pressure. The duck billed valve is retained in a housing in such a way that any instrument inserted into the valve is guided directly into the top of an endotracheal tube (or nasal mask or other interface as are known in the art), fitted at the outlet to the neonate 304. To aid in performing this, a tube guide (not shown) may be provided inside apparatus 600 which is aligned with the inlet 603 and the first outlet 604. An example arrangement is shown in FIG. 6 of US 2004/0040559.

The apparatus is preferably shaped to enable ease of use. More particularly, preferred embodiments enable one handed operation. The portion providing the first outlet 604 is wide and short and in the embodiment shown, it is cylindrical. A flange (not shown) may be provided at the first outlet 604 so that when apparatus 600 is used with a mask, the flange enables the operator to apply pressure to fluidly seal the mask to the patient's nose and/or mouth. The construction of apparatus 600 enables an operator to use a digit to occlude orifice 634 to vary pressure between the PIP and PEEP. The operator may do this by placing their thumb and middle finger about the first outlet 604 (or on an associated flange, if present) and use their index finger to seal orifice 634. The second outlet 606 is angled to allow the index finger to be in a natural position to occlude orifice 634.

The pressure regulator 634 will now be described in more detail with reference additionally to FIGS. 8A, 8B and 9.

Figure 8A:
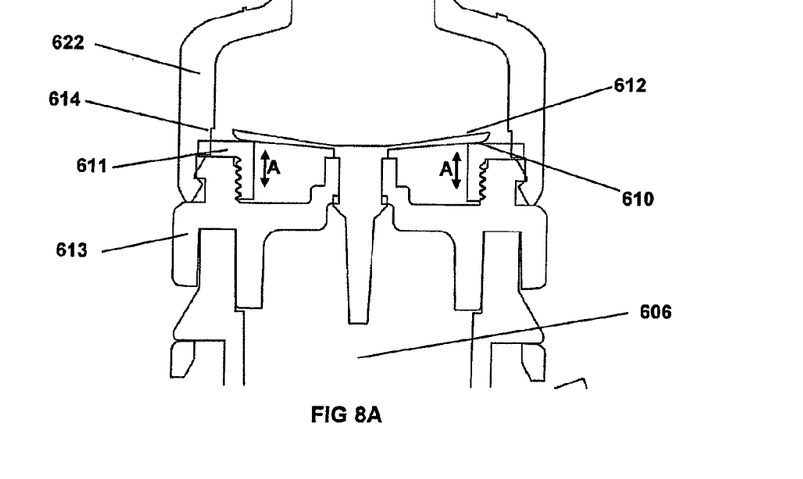
FIGS. 8A & 8B are cross-sectional views of a portion of the apparatus of FIGS. 6 & 7 in different configurations.
Figure 8B:
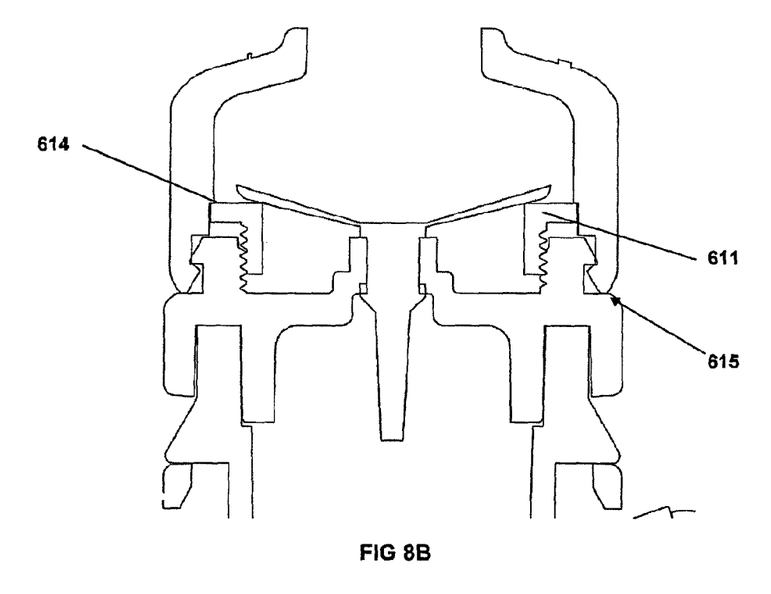
Figure 9:
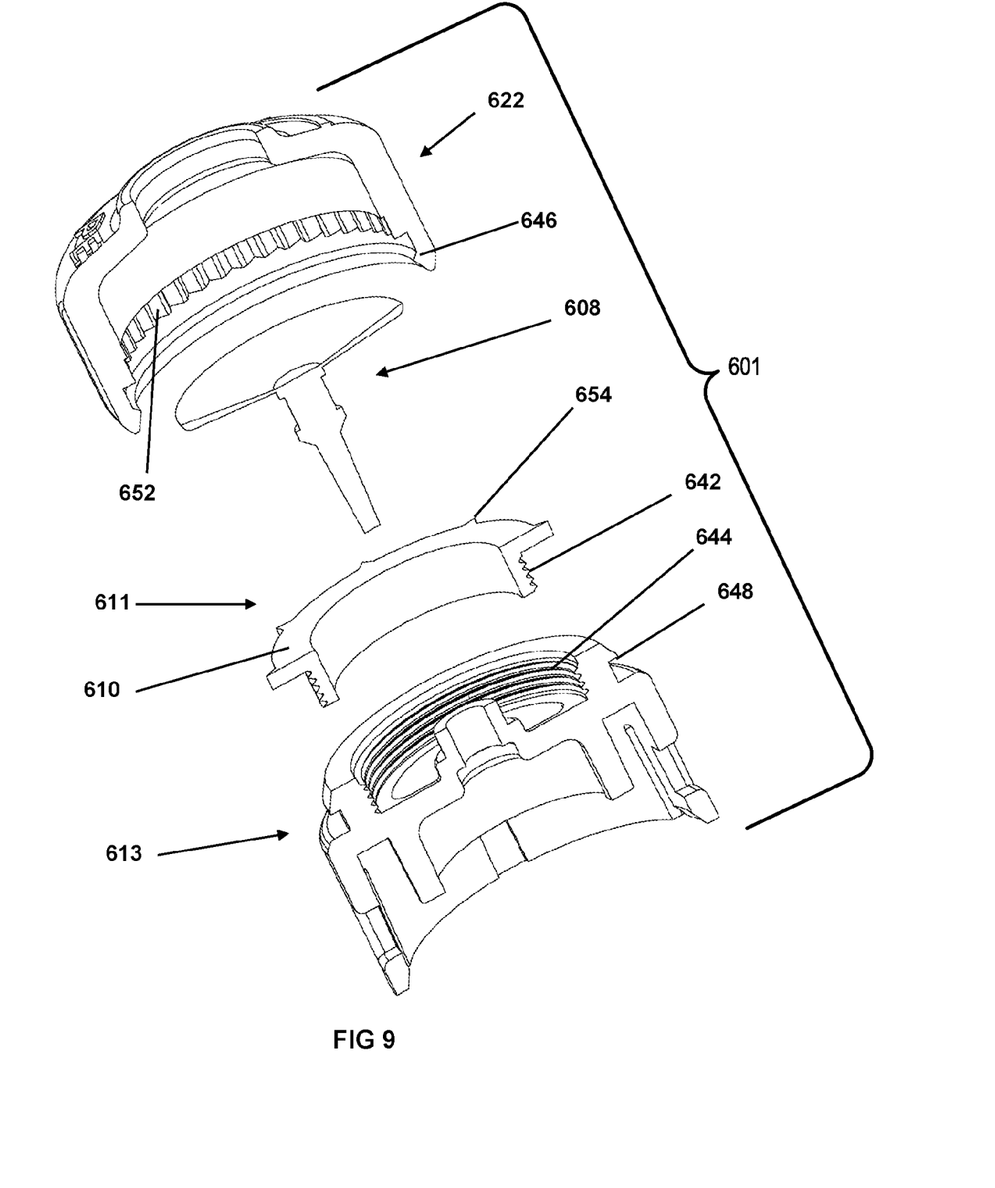
FIG. 9 is a sectional exploded view showing substantially the same portion as FIGS. 8A and 8B.

The PEEP valve 608 as shown is in the form of an umbrella valve made of an elastomeric material, positioned on a valve seat 610 (see in particular FIGS. 7 to 9). Preferably this valve is included as part of a nasal mask or endotracheal tube or other patient interface. As the flow rate increases, the skirt or flap(s) 612 of the umbrella valve lift up, thereby allowing excess pressure to be vented therethrough. Preferred embodiments provide adaptive pressure relief so as to maintain the pressure inside the apparatus 600 at a substantially constant level.

While the PEEP valve 308 is shown as an umbrella valve, the invention is not limited thereto. Other valve means may be used such as flexible diaphragms. However, umbrella valves are preferred due to the ease with which they may be fitted to or removed from the apparatus and without the need for additional fixing means, the fixing being provided by the stem portion or shaft of the umbrella valve.

While not limited thereto, according to preferred embodiments, the umbrella valve is configured in accordance with embodiments described in US 2004/0040559. More particularly, preferably, the valve is formed from Silastic liquid silicone rubber Q7-4840 and/or with dimensions as specified in FIG. 3 of US 2004/0040559 wherein the periphery of the skirt or flap(s) 612 at or proximate to the valve seat 610 is thicker than at its centre, adjacent the stem. An umbrella valve constructed in this manner does not act as a 'pop-off' valve like most umbrella valves as it is not designed to open at a specific pre-determined pressure known as the 'cracking pressure'. Rather, the valve of US 2004/0040559 is designed to open at a predetermined flow rate (e.g. below 5 liters/minute) and keep on opening as the flow rate increases causing the pressure to stay around a certain level as the flow increases. Most umbrella valves will open at a certain pressure and not open any further as the flow rate increases, causing the pressure to increase as the flow increases.

According to preferred embodiments of the invention, the tensioning of the skirt or flap(s) 612 of the PEEP valve 608 is adjustable by adjusting the relative position of the valve seat 610 as will be described in more detail below.

The pressure regulator 601 shown in FIGS. 6 to 9 includes a cap 622, seat member 611, PEEP valve 608 and mount 613.

The mount is configured to sealably couple the pressure regulator 601 to the second outlet 606. Any known coupling/sealing arrangement may be used and the invention is not limited to the specific arrangement shown. For example, rather than simply being adapted to be pushed on to the second outlet 606, a threaded, snap-fit or other form of engagement may be provided between the mount 613 and the second outlet 606. As will be appreciated O-rings and other sealing means may additionally be provided. Further, all or portions of the mount 613 may be integral to the second outlet 606 although the arrangement shown is easier to manufacture and assemble, as well as readily enabling the complete pressure regulator 601 to be removed and replaced with another, if required.

Preferably, the cap 622 sealingly engages the mount 613 to prevent gases exiting other than through the orifice 634. Preferably, this seal is provided, at least in part, at location 615 marked in FIG. 8B.

The mount 613 further positions and holds the PEEP valve 608 in position. As shown, preferably, the PEEP valve is fixed in position relative to the mount and consequently the second outlet 606, except for the skirt or flap(s) 612 which open and close to allow the PEEP valve 608 to operate.

The seat member 611 is coupled to the mount 613 so as to enable the valve seat 610 to move relative to the fixed position of the PEEP valve 608. According to the embodiment shown, an external thread 642 on the seat member 611 cooperates with an internal thread 644 on the mount 613 such that rotation of one relative to the other moves the seat member 611 as shown by the arrows marked A in FIG. 8A. While this arrangement is preferred, other means for generating the same or similar relative movement of the valve seat 610 relative to the PEEP valve 608 are included within the scope of the invention.

In FIG. 8A, the seat member 611 is in the lowermost position with the underside thereof abutting the mounting means 613. It will be appreciated that alternative arrangements may be used to limit the extent of movement in this direction. In FIG. 8B, the seat member 611 is in the uppermost position with the upper side thereof abutting projection or instep 614. Again, alternative arrangements may be used to limit the extent of movement. The seat member 611 is positionable between the lowermost and uppermost positions shown in FIGS. 8A and 8B. To maintain the position of the seat member 611 in use, preferably the threaded engagement between the seat member 611 and the mount 613 and/or the sliding engagement between the cap 622 and the mount and/or the sliding engagement between the cap and the seat member 611 generate sufficient friction to substantially prevent unwanted adjustment (i.e., adjustment not directly generated by a user rotating the cap 622). To this end, the threaded engagement may be spring-biased so as to generate forces in the directions marked A in FIG. 8A, thereby increasing the friction therebetween.

The cap 622 in the embodiment shown is configured to snap fit to the mount 613. More particularly, a lip 646 of the cap 622 engages a lip 648 of the mount 613. While not limited thereto, preferably the cap 622 is releasably fitted to enable it to be removed, thereby allowing access inside the regulator 601 such as to replace the PEEP valve 608.

The cap 622 further includes teeth 652 configured to mate with the projections 654 on the mount 613. The top or end of cap 622 terminates in orifice 634 and as shown in the markings thereon in FIG. 6, is rotatable to adjust the PEEP. More particularly, when a user rotates the cap 622, the seat member 611 also rotates since the projections 654 mate with the teeth 652 locking the cap 622 in position rotationally relative to the seat member 611. The rotation of the cap 622 generates movement in the direction A of the seat member 611 through action of the thread 642 against the thread 644. The movement of the seat member 611 is accommodated in the portion of the cap 622 that engages the mount 613. As shown, the teeth 652 are elongate, allowing the projections 654 to move in the direction A relative to the cap 622 while rotationally fixing the cap 622 relative to the mount 613.

While this arrangement is presently preferred, equivalent arrangements are also included with the scope of the invention. Further, to prevent wear of the skirt or flap(s) 612 of the PEEP valve 608 caused by rotation of the cap 622 and the seat 610, the seat 610 may be rotatably isolated from the seat member 610 such that it does not rotate.

Further, it will be appreciated that it would be possible to slidably couple the cap 622 and seat member 611 assembly to mount 613. However, the arrangement shown facilitates greater control of movement as well as providing for smaller adjustments to be made.

Thus, the invention provides a pressure regulator that provides simple, controlled adjustment of the PEEP value by hand without the need for additional equipment.

According to particular embodiments, the device of embodiments of the invention is preset during manufacture or assembly such that the cap 622 is in a desired position for generating a selected PEEP pressure or pressure profile. This can avoid the need for users to adjust the setting for more "standard" cases.

Figure 10A:
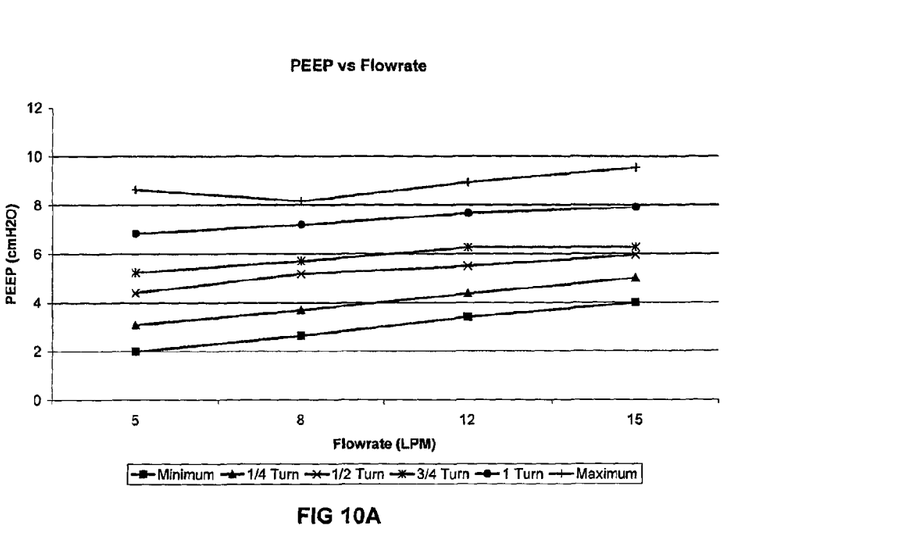
FIG. 10A is a graph comparing pressure ranges for a prototype of the present invention with the cap rotated between various positions and with flow ranging from 5 to 15 liters/minute.
Figure 10B:
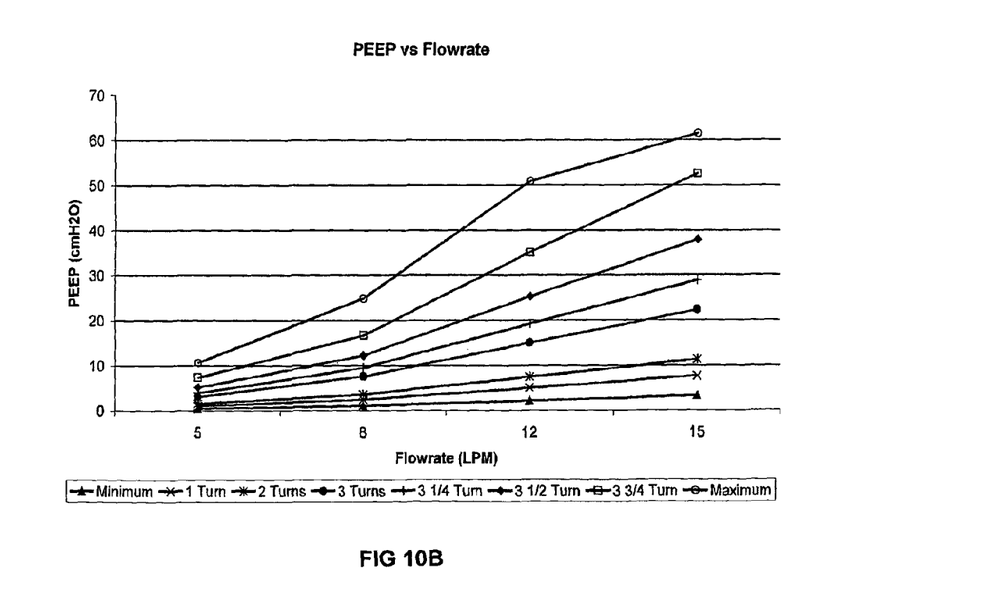
FIG. 10B is a graph comparing pressure ranges for a prior art arrangement of the type shown in FIGS. 1 and 2 with the cap rotated between various positions and with flow ranging from 5 to 15 liters/minute.

Improved results provided by the invention can be seen in FIG. 10A when compared with the results shown in FIG. 10B for a device of the type shown in FIGS. 1 and 2 (Fisher & Paykel Healthcare Limited product code RD1300-10). The results shown in FIG. 10A were generated using a prototype made in accordance with the embodiment shown in FIGS. 6-9. Flow was generated using Fisher & Paykel Healthcare Limited's Neopuff™ resuscitator, details of which are annexed hereto and incorporated herein. Pressure was measured at the base of the T-piece where the patient interface would be attached (i.e., at first outlet 604).

FIG. 10A shows how the PEEP varied as the flow rate increased from 5 to 15 liters per minute with the cap 622 in six different rotational positions. Note that the "minimum" position corresponds to that shown in FIG. 8A with the cap 622 fully wound to the left and the seat member 611 fully down. Conversely, the "maximum" position corresponds to that shown in FIG. 8B. As can be seen, even at higher flow rates, while the PEEP did increase, the increase was not significant compared to prior art arrangements. The variation in pressure across the range of flow was greatest with the cap 622 in the "minimum" position (namely 2 cmH2O) and least when the cap 622 was in the "maximum" position (namely 0.9 cmH2O), ignoring the dip at 8 cmH2O. Further, as can be seen by the lines being substantially parallel and the spacing therebetween being substantially equal, the rotation of the cap 622 was shown to vary PEEP substantially proportionally to the amount of rotation of the cap 622, providing a meaningful and intuitive change in the PEEP as a result of rotation of the cap 622.

Thus preferred embodiments of the invention are capable of providing a substantially constant or at least less varied PEEP across a range of flow rates with the PEEP being manually adjustable. Further, since the pressure flow curve at any particular position of the cap 622 is relatively flat (i.e., the PEEP does not vary significantly), any leakage between the patient interface or mask and the patient (which is common with masks during resuscitation), does not drop the PEEP in the same way that prior art devices do, preventing collapse of the patient's lungs.

Turning to the results shown in FIG. 10B, which were generated in a similar manner but with the T-piece switched over, it can be seen that the variation in PEEP across the same range of flow rates was greater for all positions of the cap. Notably, the minimum variation was recorded with the cap in the "minimum position", the PEEP differing across this range by 2.69 cmH2O, which was greater than the maximum variation of 2 cmH2O in FIG. 10A for any given position of the cap. Further, the PEEP increased more sharply when the flowrate exceeded 8 LPM, rather than the steady increase shown in FIG. 10A for the prototype according to the present invention.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the scope of the invention.

The invention claimed is:

1. A pressure regulating device for use with a breathing assistance apparatus which conveys gases along a gases pathway to a patient, the device comprising:
   a mounting for connecting the pressure regulating device to a first outlet in fluid communication with the gases pathway, the mounting configured to hold a valve member;
   a control member moveably engaged with the mounting such that manipulation of the control member adjusts a property of the valve member, wherein the property comprises a selected level of pressure;
   a seat member, whereby manipulation of the control member moves the seat member and effects said adjustment of the selected level of pressure;
   wherein a portion of the valve member sits on the seat member when a pressure of gases is below the selected level and the portion moves away from the seat member when the pressure of gases is above the selected level;
   wherein the valve member is configured to at least partially block the first outlet when the pressure of gases in the pathway is below a selected level, and allow at least a portion of said gases to flow out said first outlet when the pressure of said gases is above said selected level; and whereby manipulation of the control member adjusts the level of pressure between a maximum level and a minimum level.

2. The pressure regulating device of claim 1, wherein the control member is rotatably coupled to the mounting.

3. The pressure regulating device of claim 1, wherein the valve member comprises an elastomeric member.

4. The pressure regulating device of claim 1, wherein the valve member comprises a skirt or at least one flap, wherein said selective blocking is performed by movement of the skirt or flap(s).

5. The pressure regulating device of claim 1, wherein the valve member comprises a shaft.

6. The pressure regulating device of claim 5, wherein the valve member is coupled to the mounting by the shaft.

7. The pressure regulating device of claim 1, wherein the seat member comprises a substantially annular surface on which said portion of the valve member sits.

8. The pressure regulating device of claim 1, wherein the seat member is engaged with the control member.

9. The pressure regulating device of claim 1, configured such that manipulation of the control member moves the seat member in a direction substantially parallel to an axis of the first outlet.

10. The pressure regulating device of claim 1, wherein the control member is rotatably fixed relative to the seat member.

11. The pressure regulating device of claim 1, wherein the seat member is threadingly engaged to the mounting whereby rotation of the control member effects a movement of the seat member relative to the mounting.

12. The pressure regulating device of claim 1, wherein the control member and seat member are engaged so as to provide for sliding engagement, in a direction substantially parallel to the axis of the first outlet.

13. The pressure regulating device of claim 12, wherein the seat member comprises at least one projection configured to be received in a groove or between elongated teeth provided on the control member, the projection being slidable along the groove or between the teeth but preventing relative rotation between the control member and the seat member.

14. The pressure regulating device of claim 1, wherein the control member is in the form of a cap having a sidewall that extends from the first outlet when coupled thereto and an orifice in an endwall thereof to allow gases to be exhausted therethrough.

15. The pressure regulating device of claim 14, wherein the orifice is configured to be selectively occluded including by placement of a digit of a user thereon.

16. The pressure regulating device of claim 1, wherein, with the control member in any given position, the pressure of gases inside the gases pathway is substantially independent of the rate of flow of the gases inside the gases pathway.

17. The pressure regulating device of claim 1, wherein pressure regulating device comprises the first outlet.

18. The pressure regulating device of claim 1, wherein the mounting is at least in part integral with a wall defining the first outlet.

19. The pressure regulating device of claim 1, wherein the mounting is coupleable to a wall defining the first outlet.

20. The pressure regulating device of claim 1, comprising an inlet for receiving gases therethrough.

21. The pressure regulating device of claim 20, wherein the inlet is configured to couple to an apparatus configured to provide a flow of gas.

22. The pressure regulating device of claim 1, comprising a second outlet, the second outlet configured to deliver gas to the patient.

23. The pressure regulating device of claim 22, wherein the second outlet is coupleable to a patient interface including via a conduit.

24. The pressure regulating device of claim 22, wherein when the first outlet is blocked or substantially blocked, at least a major portion of the gases are delivered to a patient interface via the second outlet, and when the valve member is open, at least a portion of the gas is vented through the first outlet thereby providing pressure relief.

25. The pressure regulating device of claim 1, further comprising an aperture adapted to allow insertion of equipment therethrough, wherein the aperture allows insertion of a surfactant delivery means or a suction tube.

26. The pressure regulating device of claim 25, comprising sealing means adapted to prevent gas flow through said aperture and allow the equipment to be inserted therethrough while providing breathing assistance.

27. The pressure regulating device of claim 26, wherein the sealing means is a duck billed valve.

28. The pressure regulating device of claim 22, wherein the second outlet forms at least part of a patient interface.

29. The pressure regulating device of claim 1, wherein the control member includes a projection extending away from a circumference of an inner wall, the projection comprising a seating surface.

30. The pressure regulating device of claim 1, wherein the mounting is removably connected to the wall defining the first outlet.

31. The pressure regulating device of claim 1, wherein the mounting is irremovably connected to the wall defining the first outlet.

32. The pressure regulating device of claim 31, wherein at least a portion of the mounting is integral with the wall defining the first outlet.

33. A pressure regulating device for use with a breathing assistance apparatus which conveys gases along a gases pathway to a patient, the device comprising:

a mounting for supporting the pressure regulating device relative to a first outlet in fluid communication with the gases pathway;

a control member moveably engaged with the mounting such that manipulation of the control member adjusts a property of the valve member, wherein the property comprises a selected level of pressure;

a valve support member, whereby manipulation of the control member moves the valve support member relative to the control member and the mounting and effects the adjustment of the selected level of pressure;

wherein the valve member is configured to contact a valve seat to at least partially block the first outlet when the pressure of gases in the pathway is below a selected level, and to move away from the valve seat when the pressure of the pressure of the gases in the pathway is above the selected level to allow at least a portion of said gases to flow out the first outlet when the pressure of the gases is above the selected level; and whereby manipulation of the control member adjusts the level of pressure between a maximum level and a minimum level.

34. The pressure regulating device of claim 33, wherein the valve seat is defined by a substantially annular surface of a seating projection on which the portion of the valve member sits.

35. The pressure regulating device of claim 34, wherein the valve support member comprises the seating projection.

36. The pressure regulating device of claim 33, further configured such that manipulation of the control member moves the valve support member in a direction aligned with an axis of the first outlet.

37. The pressure regulating device of claim 33, wherein the control member is rotatably fixed relative to the valve support member.

38. The pressure regulating device of claim 33, wherein the valve support member is threadingly engaged with the mounting.

39. The pressure regulating device of claim 33, wherein the control member and valve support member are engaged so as to provide for sliding engagement, in a direction substantially aligned with the axis of the first outlet.

40. The pressure regulating device of claim 33, wherein the valve support member further comprises at least one projection configured to be received in a groove or between elongated teeth provided on the control member, the projection being slidable along the groove or between the teeth but preventing relative rotation between the control member and the valve support member.

41. The pressure regulating device of claim 33, further comprising an aperture adapted to allow insertion of equipment therethrough, wherein the aperture allows insertion of a surfactant delivery means or a suction tube.

42. The pressure regulating device of claim 33, comprising a seal adapted to prevent gas flow through said aperture and allow the equipment to be inserted therethrough while providing breathing assistance.

* * * * *